United States Patent [19]

van der Zel

[11] Patent Number: 4,735,772

[45] Date of Patent: Apr. 5, 1988

[54] PALLADIUM-COBALT ALLOYS; MANUFACTURE OF A ROOT CAP

[75] Inventor: Joseph M. van der Zel, Le Hoorn, Netherlands

[73] Assignee: Elephant Edelmetaal B.V., Le Hoorn, Netherlands

[21] Appl. No.: 934,906

[22] Filed: Nov. 25, 1986

[30] Foreign Application Priority Data

Nov. 27, 1985 [NL] Netherlands .................. 8503284

[51] Int. Cl.$^4$ .................. C22C 5/04; C22C 19/07; C22C 30/00
[52] U.S. Cl. .................. 420/440; 420/463; 420/465; 420/583; 420/585; 433/207
[58] Field of Search .............. 420/463, 464, 465, 440, 420/583, 585; 433/207

[56] References Cited

U.S. PATENT DOCUMENTS

| | | | |
|---|---|---|---|
| 2,226,079 | 12/1940 | Spanner | 420/35 |
| 3,928,913 | 12/1975 | Schaffer | 420/465 |
| 4,382,909 | 5/1983 | Zwingmann | 420/463 |
| 4,387,072 | 6/1983 | Schaffer | 420/464 |
| 4,451,639 | 5/1984 | Prasad | 420/464 |

FOREIGN PATENT DOCUMENTS

| | | | |
|---|---|---|---|
| 0036556 | 9/1981 | European Pat. Off. | |
| 684186 | 11/1939 | Fed. Rep. of Germany | |
| 62937 | 5/1981 | Japan | 420/463 |
| 156731 | 12/1981 | Japan | 420/463 |

*Primary Examiner*—L. Dewayne Rutledge
*Assistant Examiner*—Robert L. McDowell
*Attorney, Agent, or Firm*—Stevens, Davis, Miller & Mosher

[57] ABSTRACT

The invention relates to magnetic Pd-Co alloys for use in dental prostheses, in particular in root caps. The alloys contain, by weight, 40–60% Pd, 20–59% Co, 0–40% Ni, 0.1–5% Cr, 0.05–0.2% Re, 0.01–0.5% Fe, 0.5–3% Ga, 0–0.1% B, 0–5% Pt or Au, and the gallium may be replaced, in full or in part, by Sn, In, Zn or Mn.

14 Claims, No Drawings

PALLADIUM-COBALT ALLOYS; MANUFACTURE OF A ROOT CAP

This invention relates to palladium-cobalt alloys containing 40–60% by weight of Pd, 20–59% by weight of Co and 0–40% by weight of Ni. The invention also relates to a method of making a root cap from a cast palladium-cobalt alloy.

Kinouchi et al., J. Dent. Res. (60) 1, 50–58 (1981) have described palladium-cobalt alloys which in combination with samarium-cobalt magnets can be used in dentistry for magnetically retaining dental prostheses. Sm-Co magnets, or in general rare earth-cobalt magnets have proved to be suitable in dimensions as small as in the millimeter range for use in prostheses; see for example Netherlands patent No. 163,713. As, however, the material cannot be cast, the shapes are generally limited to disks, columns or prisms. As a consequence, it is rarely possible to make the magnet in a form suitable for individual cases.

To overcome these problems, there has been a search for ferromagnetic alloys which could replace the magnet in the live tissue. Ferromagnetic alloys exhibit magnetic characteristics like those of soft iron. It is important that the alloys should be castable. Ferromagnetic properties and castability can solve the above problems. The magnet in the root can then be replaced by a cast root cap. In this case the magnetic attraction between the samarium-cobalt magnet in the prosthesis and the alloy in the root is used for retention of the prosthesis, for example, dentures. In addition to having ferromagnetism and being castable, the alloy should also have physical and chemical properties which render it suitable for use in the mouth. Known alloys, however, have poor castability and low corrosion resistance, so that they cannot be used as a dental cast metal.

Although nearly all conventional dental alloys are non-ferromagnetic, stainless steel containing 13 or 18 percent chromium, and cobalt-chromium and nickel-chromium alloys are ferromagnetic. Stainless steel, however, has a poor castability, and the ferromagnetism of the other two alloys is too weak for them to be used for magnetic retention of dental prostheses.

In the above publication by Kinouchi et al., palladium-cobalt alloys are proposed for this purpose. The authors describe three alloys, namely 43Pd-57Co; 41 Pd-54Co-5Cr; and 43Pd-27 Co-31Ni (the numbers represent percent by weight). These alloys have the following magnetic characteristics:

| | |
|---|---|
| Maximum permeability $\mu$m | 150–280 |
| Saturation flux density $B_{100}$, kG | 6.7–10.2 |
| Residual flux density $B_r$, kG | 1.9–2.8 |
| Coercive force $H_c$, Oersted | 5.3–6.6 |

The melting point of these alloys ranges between 1185° and 1212° C. They can be molten at the normal melting temperature in a ceramic crucible and cast in phosphate-bonded embedding composition. Corrosion tests in $Na_2S$ solution have shown that the sensitivity to sulfide attack is equal to that of the conventional gold-silver-palladium alloys used in dentistry, and is even less than with nickel-chromium alloys. These alloys, however, have the following disadvantages with regard to casting:

as a result of the contraction of the alloy during solidification and cooling, the embedding composition, which does not contract at a temperature above 650° C., exerts a force to which these alloys are not resistant. The result is that cracks are formed in the casting.

during casting, the alloys absorb gas, which during solidification is released again. This leads to blow holes and porosities in the metals, which has an adverse effect on strength, esthetics and corrosion resistance.

In Japanese patent publication No. 82-201035, magnetic palladium-cobalt-nickel dental alloys are proposed, which are claimed not to crack during casting. These alloys contain 20–40% by weight of cobalt, 20–40% by weight of nickel, 25–60% by weight of palladium, and minor proportions of molybdenum, iridium, chromium, indium and zinc. In them, molybdenum, chromium and indium are used for their grain refining and deoxidizing effect. Iridium is also used to obtain a fine-grained structure. Zinc is used to improve castability.

In practice, however, it is found that these known alloys yet exhibit cracks after casting, especially if they are cast at somewhat higher temperatures. Also, many blow holes and considerable porosity are found, and cold deformability is poor.

It is an object of the present invention to provide castable ferro-magnetic alloys suitable for use in dentistry and lacking the above disadvantages of known alloys.

This object is realized, according to the present invention, with palladium-cobalt alloys containing 40–60% by weight of Pd, 20–59% by weight of Co, and 0–40% by weight of Ni, characterized by containing
- 0.1–5% by weight of chromium,
0.05–0.2% by weight of rhenium,
0.01–0.5% by weight of iron,
0.5–3% by weight of at least one element selected from the group consisting of gallium, tin, indium, zinc, and manganese,
0–0.1% by weight of boron,
0–5% by weight of at least one of the metals selected from the group consisting of platinum and gold,
and possibly other elements, whether present as impurities or deliberately added, in such small quantities that they do not essentially adversely affect the properties of the alloys.

It has been found that, in palladium-cobalt alloys, rhenium is a much more effective grain refiner than iridium, which apparently is dissolved in the palladium. A rhenium concentration of 0.05–0.2% by weight has proved to be very suitable. Preferably, about 0.1% by weight of rhenium is used.

To realize a good cold deformability of the alloys, iron should be present in addition to rhenium. If the alloys contain 0.01–0.5% by weight of iron, the combination of rhenium and iron surprisingly leads to such a suitable fine-grained structure that a good cold deformation is possible. Preferably, the alloys contain 0.05–0.3% by weight of iron. In that case, a reduction in diameter of 90% can be accomplished by cold rolling without the occurrence of cracking. In known alloys, cracks occur already if the reduction in diameter during cold deformation exceeds a value of 45%.

The presence of 0.5–3% by weight of gallium leads to a lower melting temperature, to better castability without the formation of porosity, and to higher strength at high temperatures. The elements zinc and indium, present in known alloys, also lead to a lower melting temperature, it is true, but they also lead to lower strength at high temperatures. Nevertheless, in the alloys according to the invention, gallium can be replaced, in full or in part, by tin, indium, zinc or manganese.

The alloys according to the invention contain chromium and optionally boron for their deoxidizing activity. Owing to their high affinity to oxygen, these elements neutralize the formation of gaseous products in the melt, as a result of which porosity is fully prevented. The proportion of boron may be 0–0.1% by weight, but is preferably 0.005–0.1% by weight, and most preferably 0.01–0.03% by weight. The proportion of chromium may be 0.1–5% by weight. When the chromium content is relatively high, however, a chromium oxide slag tends to form on the melt, which makes it difficult to estimate the correct moment of casting, and the chance of oxide inclusions in the alloys is increased. At relatively low chromium concentrations, however, the chance of porosity is increased. Accordingly, the chromium content is preferably 0.1–1.0% by weight, and most preferably 0.2–0.7% by weight. An excellently suitable chromium content is about 0.4% by weight.

The alloys may contain 0–40% by weight of nickel, but in preactice alloys which do not contain nickel are preferred. To improve corrosion resistance, it may be attractive to replace 0–5% of the palladium by platinum or gold, which, however, does make the alloy more expensive.

The alloys according to the invention can be used in dentistry to retain prostheses, such as dentures, in position in cooperation with one or more permanent magnets, such as Sm-Co magnets. By virtue of their castability, they can be brought into a form suitable for each individual case, for example, in the form of a root cap. In this connection reference is made to the above article by Kinouchi et al.

EXAMPLE

The pure metals, such as palladium of 99.9%, electrolytic cobalt, rhenium of 99.9%, iron of 99%, gallium of 99.99%, and boron, were molten together in a Zirconia crucible in an induction oven under vacuum. The composition was:

| | | |
|---|---|---|
| Palladium | 50 | percent |
| Cobalt | 47.2 | percent |
| Chromium | 0.4 | percent |
| Rhenium | 0.1 | percent |
| Gallium | 2.2 | percent |
| Iron | 0.08 | percent |
| Boron | 0.02 | percent. |

After casting, the cast turned out to be free from hair cracks and porosities. The magnetic characteristics were as follows:

| | |
|---|---|
| Maximum permeability $\mu$m | 240 |
| Saturation flux density $B_{100} \cdot kG$ | 10.0 |
| Residual flux density $B_{100} \cdot kG$ | 2.5 |
| Coercive force $H_o$, Oersted | 5.7 |

The physical properties were as follows:

| | |
|---|---|
| Melting interval, °C. | 1195–1210 |
| Vicker's hardness (after casting) kg/mm$^2$ | 305 |
| Tensile strength (after casting) daN/mm$^2$ | 80 |
| Yield point (after casting), daN/mm$^2$ | 70 |
| Elongation at break (after casting), % | 15 |

In the following table, a number of alloys according to the present invention (Nos. 5–8) are compared with some known alloys.

TABLE

| Example | Pd | Co | Ni | Cr | Mo | In | Zn | Ir | Re | Ga | Fe | B | average particle size μm | cracks | porosity | oxide inclusions |
|---|---|---|---|---|---|---|---|---|---|---|---|---|---|---|---|---|
| 1** | 43 | 57 | — | — | — | — | — | — | — | — | — | — | 175 | yes | yes | moderate |
| 2** | 41 | 54 | — | 5 | — | — | — | — | — | — | — | — | 180 | yes | less | yes, many |
| 3** | 43 | 27 | 30 | — | — | — | — | — | — | — | — | — | 150 | yes | yes | moderate |
| 4* | 43 | 25 | 25 | 2.9 | 0.5 | 1.5 | 2.0 | 0.1 | — | — | — | — | 95 | less | less | yes, many |
| 5 | 43 | 53.9 | — | 0.4 | — | — | — | — | 0.1 | 2.5 | 0.08 | 0.02 | 22 | no | no | no |
| 6 | 41 | 52.0 | — | 5 | — | — | — | — | 0.1 | 1.8 | 0.08 | 0.02 | 25 | no | no | yes, many |
| 7 | 43 | 27 | 28 | 0.5 | — | — | — | — | 0.1 | 1.3 | 0.08 | 0.02 | 20 | no | no | no |
| 8 | 50 | 47.2 | — | 0.4 | — | — | — | — | 0.1 | 2.2 | 0.08 | 0.02 | 21 | no | no | no |

*Japanese patent publication 82-201035
**See J. Dent. Res. (60) 1.50–58, (1981)

What I claim:

1. Palladium-cobalt alloys consisting essentially of, by weight,
    40–60% palladium,
    20–59% cobalt,
    0–40% nickel,
    0.1–5% chromium,
    0.5–0.2% rhenium,
    0.01–0.5% iron
    0.5–3% of at least one element selected from the group consisting of gallium, tin, indium, zinc and manganese,
    0–0.1% boron, and
    0–5% of at least one metal selected from the group consisting of platinum and gold.

2. Palladium-cobalt alloys as claimed in claim 1, characterized by not containing nickel.

3. Palladium-cobalt alloys as claimed in claim 1, containing 0.1–1.0% by weight of chromium.

4. Palladium-cobalt alloys as claimed in claim 1, containing 0.05–0.3% by weight of iron.

5. Palladium-cobalt alloys as claimed in claim 1, containing 0.005–0.1% by weight of boron.

6. Palladium-cobalt alloys as claimed in claim 1, containing 0.5–3% by weight of gallium.

7. Palladium-cobalt alloys as claimed in claim 1, containing 0.2–0.7% by weight of chromium.

8. Palladium-cobalt alloys as claimed in claim 1, containing 0.01–0.03% by weight of boron.

9. A root cap made from an alloy as claimed in claim 1.

10. A root cap made from an alloy as claimed in claim 2.

11. A root cap made from an alloy as claimed in claim 3.

12. A root cap made from an alloy as claimed in claim 4.

13. A root cap made from an alloy as claimed in claim 5.

14. A root cap made from an alloy as claimed in claim 6.

* * * * *

UNITED STATES PATENT AND TRADEMARK OFFICE
CERTIFICATE OF CORRECTION

PATENT NO. : 4,735,772

DATED : April 5, 1988

INVENTOR(S) : Joseph M. VAN DER ZEL

It is certified that error appears in the above-identified patent and that said Letters Patent is hereby corrected as shown below:

Claim 1, line 7 (Column 4, line 36), "0.5" should be --0.05--.

Signed and Sealed this

Twenty-seventh Day of September, 1988

Attest:

DONALD J. QUIGG

Attesting Officer

Commissioner of Patents and Trademarks